United States Patent
Harkins

(10) Patent No.: US 10,639,260 B1
(45) Date of Patent: May 5, 2020

(54) LIP BALM COMPOSITION

(71) Applicant: Linda Harkins, Payson, AZ (US)

(72) Inventor: Linda Harkins, Payson, AZ (US)

( * ) Notice: Subject to any disclaimer, the term of this patent is extended or adjusted under 35 U.S.C. 154(b) by 0 days.

(21) Appl. No.: 16/254,117

(22) Filed: Jan. 22, 2019

(51) Int. Cl.
*A61K 36/185* (2006.01)
*A61K 8/49* (2006.01)
*A61K 8/02* (2006.01)
*A61Q 19/00* (2006.01)
*A61K 8/34* (2006.01)
*A61K 8/92* (2006.01)
*A61K 8/35* (2006.01)
*A61K 8/9789* (2017.01)

(52) U.S. Cl.
CPC ............ *A61K 8/498* (2013.01); *A61K 8/0216* (2013.01); *A61K 8/34* (2013.01); *A61K 8/35* (2013.01); *A61K 8/927* (2013.01); *A61K 8/9789* (2017.08); *A61Q 19/001* (2013.01)

(58) Field of Classification Search
CPC .................................................. A61K 36/185
See application file for complete search history.

(56) References Cited

U.S. PATENT DOCUMENTS

| | | |
|---|---|---|
| 5,503,825 A | 4/1996 | Lane |
| D443,951 S | 6/2001 | Look |
| 8,425,950 B1 | 4/2013 | Santillan |
| 8,425,954 B2 | 4/2013 | Stone |
| 2006/0188315 A1 | 8/2006 | Look |
| 2012/0021075 A1 | 1/2012 | Umanskaya |
| 2012/0164087 A1* | 6/2012 | Carter ................ A61K 8/64 424/60 |
| 2013/0142881 A1 | 6/2013 | Odom |
| 2013/0274321 A1 | 10/2013 | Newland |

* cited by examiner

*Primary Examiner* — Rosanne Kosson

(57) ABSTRACT

A lip balm composition includes a composition including petroleum jelly, camphor, menthol, phenol, beeswax, and *cannabis*.

10 Claims, No Drawings

LIP BALM COMPOSITION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98.

The disclosure and prior art relates to lip balms and more particularly pertains to a new lip balm for delivering active THC to a person's lips.

BRIEF SUMMARY OF THE INVENTION

An embodiment of the disclosure meets the needs presented above by generally comprising a composition including petroleum jelly, camphor, menthol, phenol, beeswax, and *cannabis*.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

Not Applicable

DETAILED DESCRIPTION OF THE INVENTION

With reference now to disclosure below, a new lip balm embodying the principles and concepts of an embodiment of the disclosure will be described.

As best illustrated in FIGS. 1 through 6, the lip balm composition is a generally conventional lip balm that may be used for treating lips and, in the present invention, provide a delivery mechanism for tetrahydrocannabinol, also known as THC, found in *cannabis*. The source of the *cannabis* includes typical plant varietals such as *Cannabis sativa*, *Cannabis indica*, and *Cannabis ruderalis*. As such, the composition may be used for treating other ailments conventionally treated with THC.

The composition further includes petroleum jelly, camphor, menthol, phenol, and beeswax. Each of these is readily available and widely known, but each will be further explained below.

Petroleum jelly, which is also known as petrolatum, white petrolatum or soft paraffin, is a ubiquitously found ingredient of semi-solid hydrocarbons. White petroleum is used often in lip balms, as is beeswax, to help form a layer over the lips to seal in moisture. Beeswax, also known as cera alba and containing several chemical compounds including triacontanyl palmitate, is also easily found and mixed with the white petroleum to form a base of the lip balm composition.

Camphor, 1,7,7-Trimethylbicyclo[2.2.1]heptan-2-one, is a waxy, solid added for aroma and which is produced by the camphor laurel, *Cinnamomum camphora*. Menthol, 5-Methyl-2-(propan-2-yl)cyclohexan-1-ol, is used as a local anesthetic and is producible synthetically or naturally from corn mint, peppermint or other mint oils.

The composition further contains *cannabis* such that the amount of THC within the composition is at least 3%. Generally, the upper limit of the total concentration of THC in the composition is 6% but higher amounts are possible, however such may detract the composition functioning as a skin protectorate.

An example of the composition may include, by volume:
15% to 25% petroleum jelly;
3% to 7% camphor;
3% to 7% menthol;
3% to 7% phenol;
40% and 50% beeswax; and
15% and 25% *cannabis* having a THC concentration of between 15% and 30% THC.

In another embodiment of the composition, the composition includes by volume:
20% petroleum jelly;
5% camphor;
5% menthol;
5% phenol;
45% beeswax; and
20% *cannabis* having a THC concentration of between 15% and 30% THC.

In use, the composition may be presented in a small container or within a conventional lip balm dispenser. The composition is applied to a person's lips to protect the lips while the THC may absorbed through the lining of the mouth and ingestion. However, localized effects on the lips themselves, such as reduced inflammation and pain, is achieved by absorption directly into the skin.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A lip balm composition configured for positioning on a person's lips, said lip balm comprising:
   petroleum jelly;
   camphor;
   menthol;
   phenol;
   beeswax; and
   *cannabis*.

2. The lip balm composition according to claim 1, wherein said *cannabis* contains a THC concentration of at least 15%.

3. The lip balm composition according to claim 2, wherein said composition comprises by volume between 15% and 25% of said *cannabis*.

4. The lip balm composition according to claim 3, wherein said *cannabis* contains a THC concentration of less than 30%.

5. The lip balm composition according to claim 4, wherein said composition comprises by volume between 15% and 25% of said petroleum jelly.

6. The lip balm composition according to claim 4, wherein said composition comprises by volume between 3% and 7% of said camphor.

7. The lip balm composition according to claim 4, wherein said composition comprises by volume between 3% and 7% of said menthol.

8. The lip balm composition according to claim 4, wherein said composition comprises by volume between 3% and 7% of said phenol.

9. The lip balm composition according to claim 4, wherein said composition comprises by volume between 40% and 50% of said beeswax.

10. A lip balm composition configured for applying to a person's lips; said lip balm comprising by volume:
    15% to 25% petroleum jelly;
    3% to 7% camphor;
    3% to 7% menthol;
    3% to 7% phenol;
    40% and 50% beeswax; and
    15% and 25% *cannabis* having a THC concentration of between 15% and 30% THC.

\* \* \* \* \*